United States Patent [19]

Haber et al.

[11] Patent Number: 5,211,285
[45] Date of Patent: May 18, 1993

[54] TELESCOPING, PHARMACEUTICAL MIXING CONTAINER

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 853,688

[22] Filed: Mar. 19, 1992

[51] Int. Cl.⁵ .................... B65D 25/08; A61M 37/00; A61M 5/315; G01F 19/00
[52] U.S. Cl. .................................. 206/221; 604/82; 604/231; 604/208; 73/429
[58] Field of Search .................. 604/903, 208, 231, 82, 604/191; 206/221, 219; 73/429

[56] References Cited

U.S. PATENT DOCUMENTS

| | | | |
|---|---|---|---|
| 2,660,342 | 11/1953 | Ruf | 73/429 |
| 4,968,299 | 11/1990 | Ahlstrand et al. | 604/191 X |
| 4,973,318 | 11/1990 | Holm et al. | 604/208 |
| 5,015,229 | 5/1991 | Meyer et al. | 604/231 X |
| 5,017,190 | 5/1991 | Simon et al. | 604/208 |
| 5,080,649 | 1/1992 | Vetter | 604/208 |

FOREIGN PATENT DOCUMENTS 1212823 11/1970 United Kingdom ................ 604/208
2229374 9/1990 United Kingdom ................ 604/191

Primary Examiner—William I. Price
Attorney, Agent, or Firm—Townsend and Townsend Khourie and Crew

[57] ABSTRACT

A telescoping, pharmaceutical mixing container (2) includes outer and inner containers (4, 6) telescopically mounted to one another with the inner end (16) of the inner container situated within the outer container. The inner container has a piston cap (28) mounted to it so to provide a piston-like seal between the inner and outer containers, and houses a piston (22) within its interior. The piston cap defines a flow path (32) between first and second variable volume regions (34, 36) within the inner and outer containers respectively. Reciprocating the inner container within the outer container causes the pharmaceutical (38) to pass through the flow path and between the variable volume regions and mix. The mixing container is preferably used with a metering assembly (52) including a metering stop (74), threadably positionable along the axis (25) of the mixing container, and a driver (70) secured to the inner container. The driver includes a drive stop (72) which engages the metering stop once the inner container has moved an appropriate distance towards its collapsed condition, typically during an injection.

19 Claims, 9 Drawing Sheets

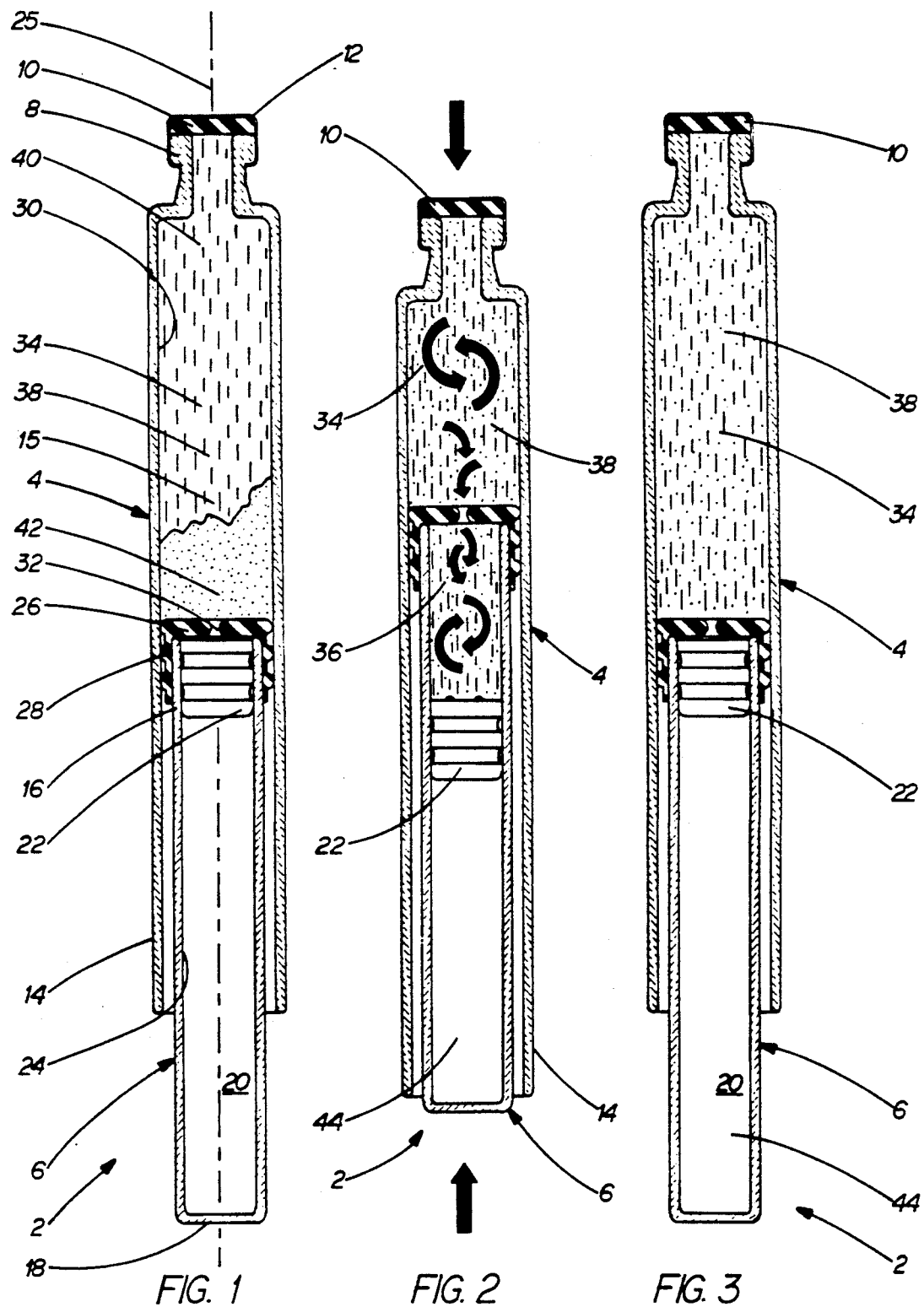

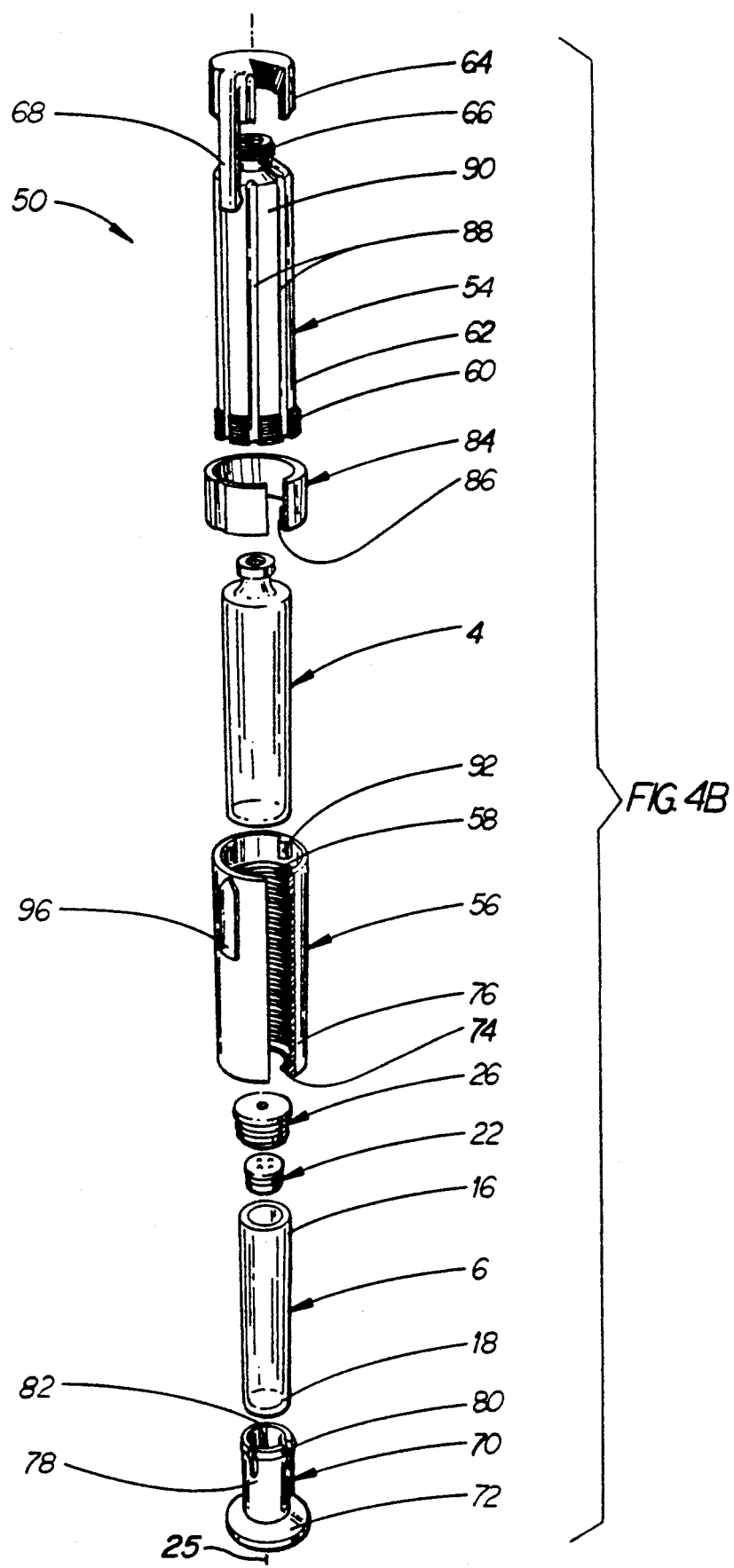

TELESCOPING, PHARMACEUTICAL MIXING CONTAINER

BACKGROUND OF THE INVENTION

Some pharmaceuticals need to be thoroughly mixed before they are administered to the patient. For example, crystals commonly form within liquid NPH insulin during storage. It is therefore very important that the NPH insulin be thoroughly mixed and agitated so that the crystals redissolve and/or become suspended within the aqueous component of the insulin prior to injection.

Certain medicines, in particular insulin, is generally self-administered by a patient. In some circumstances this can create psychological problems for the patient. A stigma of abnormality can be created in the mind of the insulin patient when conventional syringes must be used to administer the insulin.

SUMMARY OF THE INVENTION

The present invention is directed a telescoping, pharmaceutical mixing container which thoroughly and effectively agitates and mixes a liquid pharmaceutical in a container, the container preferably configured to be used as a pharmaceutical cartridge from which an injection can be given.

The telescoping, pharmaceutical mixing container includes outer and inner containers telescopically mounted to one another with the inner container passing through an open, second end of the outer container. The inner end of the inner container preferably has a piston cap mounted to it so to provide a seal between the outer surface of the inner container and the inner surface of the outer container. The inner container has a freely movable piston mounted within its interior. Preferable, the piston cap defines a flow path which fluidly couples a first variable volume region, defined within the outer container between the piston cap and the first, closed end of the outer container, and a second variable volume region, defined within the inner container between the piston cap and the piston. Moving the inner container between its telescopically extended and collapsed positions causes the liquid pharmaceutical within the two variables volume regions to pass between the variable volume regions, thus mixing a turbulent manner, while causing the piston within the inner container to reciprocate back and forth within the inner container. By making the outer end of the inner container sealed, movement of the piston towards the outer end causes any gas within the outer end to be compressed; the compressed gas acts as a spring on the piston tending to return the inner container to its extended position, thus aiding mixing.

Preferably, the mixing container is used with a metering assembly including a metering stop positionable along the axis of the mixing container and a driver secured to the inner container. The drive includes a drive stop which engages the metering stop once the inner container has moved an appropriate distance towards its collapsed condition, such as during an injection. The axial movement of the metering stop positioner is preferably through the threaded engagement of an outer sleeve, which carries the metering stop, with an inner sleeve. The inner sleeve is mounted to the outer container. The rotation of the outer sleeve relative to the inner sleeve is preferably indicated tactically and aurally by a radially inwardly extending detect carried by the outer sleeve engaging axially extending grooves formed on the outer surface of the inner sleeve.

A primary advantage of the invention is that in addition to providing through and complete mixing of the pharmaceutical, the mixing container may be used as the cartridge from the which the injection is given. In addition, when the piston is used to compress a gas within the inner container, mixing of the pharmaceutical is made easier since the inner telescoping container springs back towards its extended position naturally. Only the force of compression need be applied to the telescoping containers; they need not be pulled apart to cause the reverse movement.

When the mixing container is used with the metering assembly the entire unit provides an attractive, pen-like structure which is easy to use and allows the user to accurately and simply meter each dose. The combined assembly can be made to look much like a fountain pen permitting the assembly to be easily accessible and yet substantially eliminate any stigma of abnormality. The metering assembly can also be used as a part of a conventional syringe by replacing the inner container and piston cap by a generally conventional piston and stem.

Other features and advantages will appear from the following description in which the preferred embodiment has in set forth in detail in conjunction with the accompanying drawings.

BRIEF DESCRIPTION OF THE DRAWINGS

FIG. 1 is a cross-sectional view of a telescoping, pharmaceutical mixing container with the inner container in the extended position prior to mixing;

FIG. 2 illustrates the container of FIG. 1 with the inner container in the collapsed position and showing the mixing of the pharmaceutical;

FIG. 3 shows the container of FIG. 2 after the inner container has returned to the extended position of FIG. 1 with any solid constituents of the pharmaceutical redissolved into and/or dispersed within the liquid component;

FIGS. 4A and 4B are isometric and exploded isometric views of the mixing container of FIG. 1 together with a metering assembly;

DESCRIPTION OF THE PREFERRED EMBODIMENT

Figure 4A:
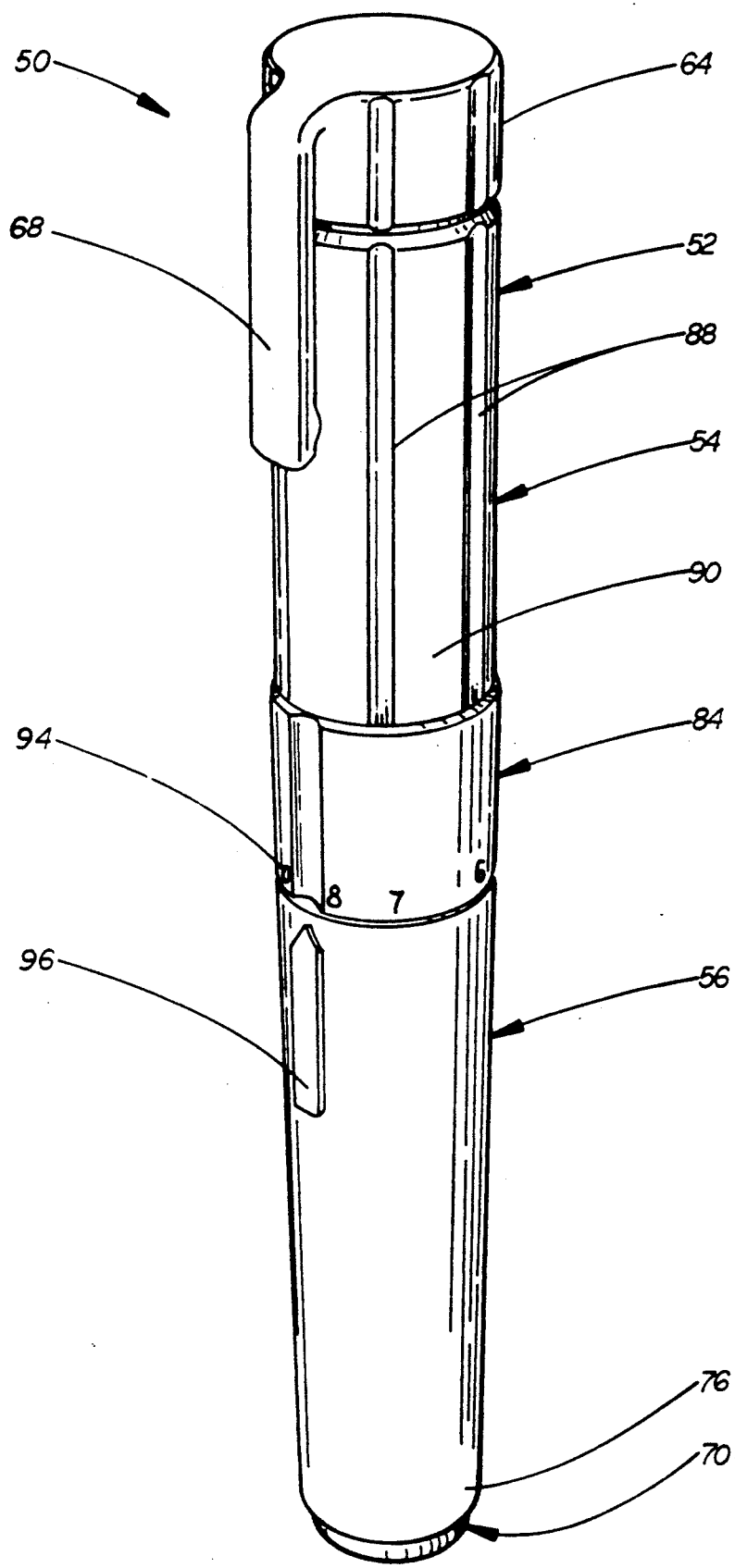
Figure 4C:
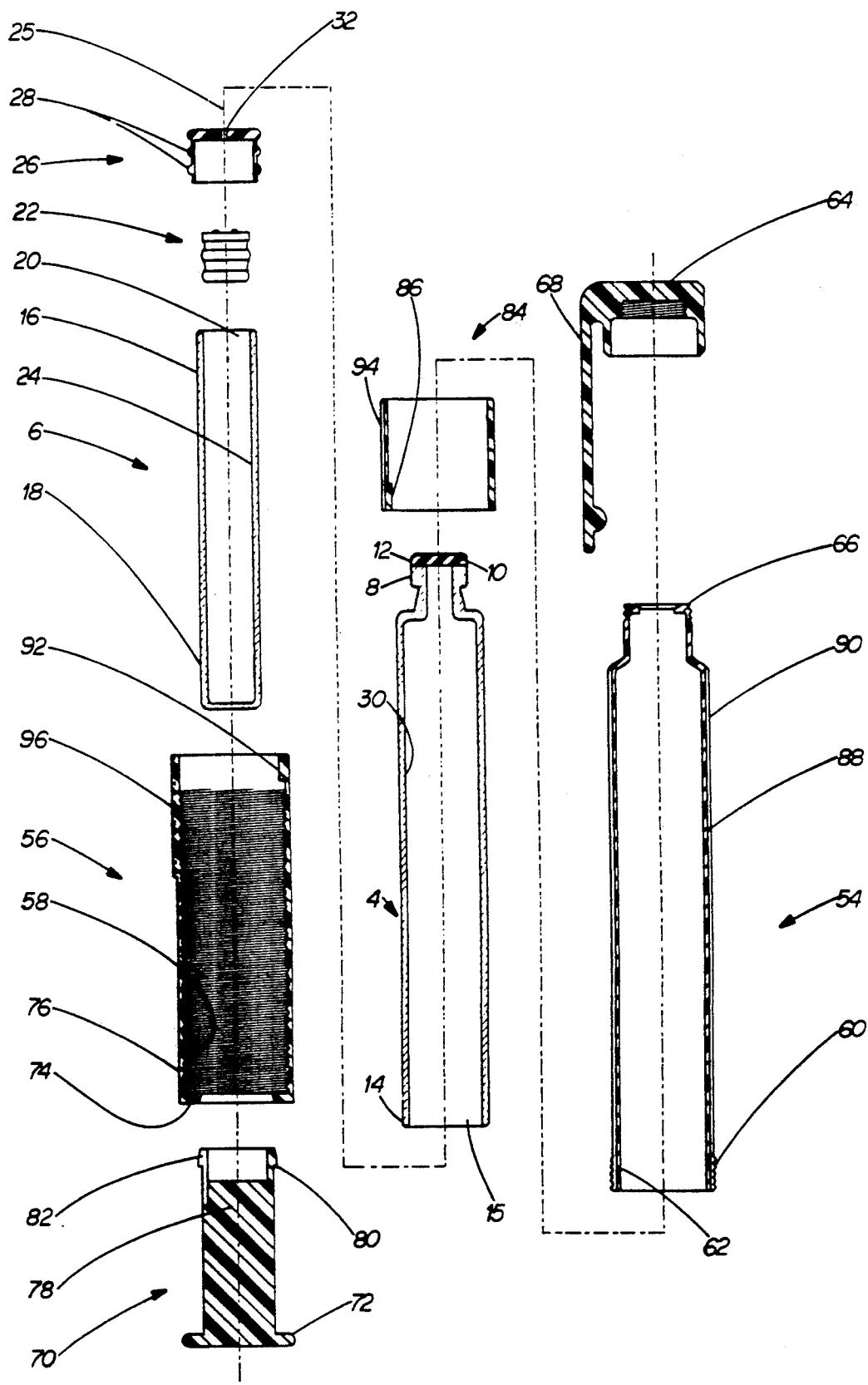
FIG. 4C is an exploded cross-sectional view of the combined mixing container with metering assembly of FIG. 4B.
Figure 5A:
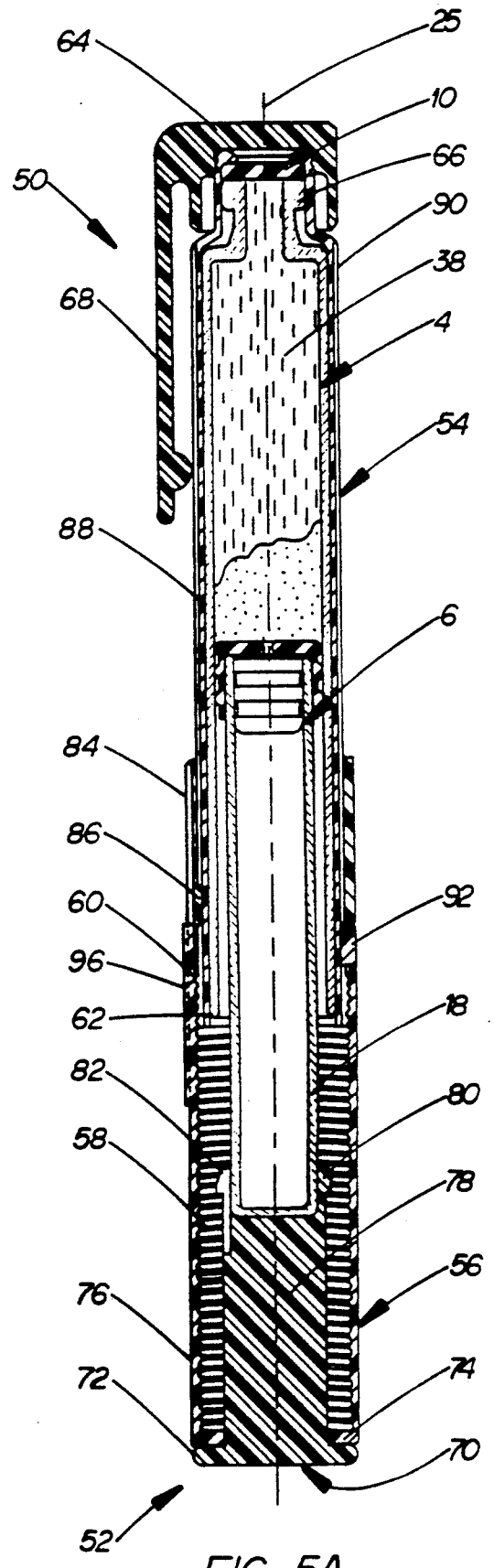
FIG. 5A shows the combined mixing container with metering assembly of FIG. 4A in an assembled, as-shipped condition with the inner container in the extended position of FIG. 1.
Figure 5B:
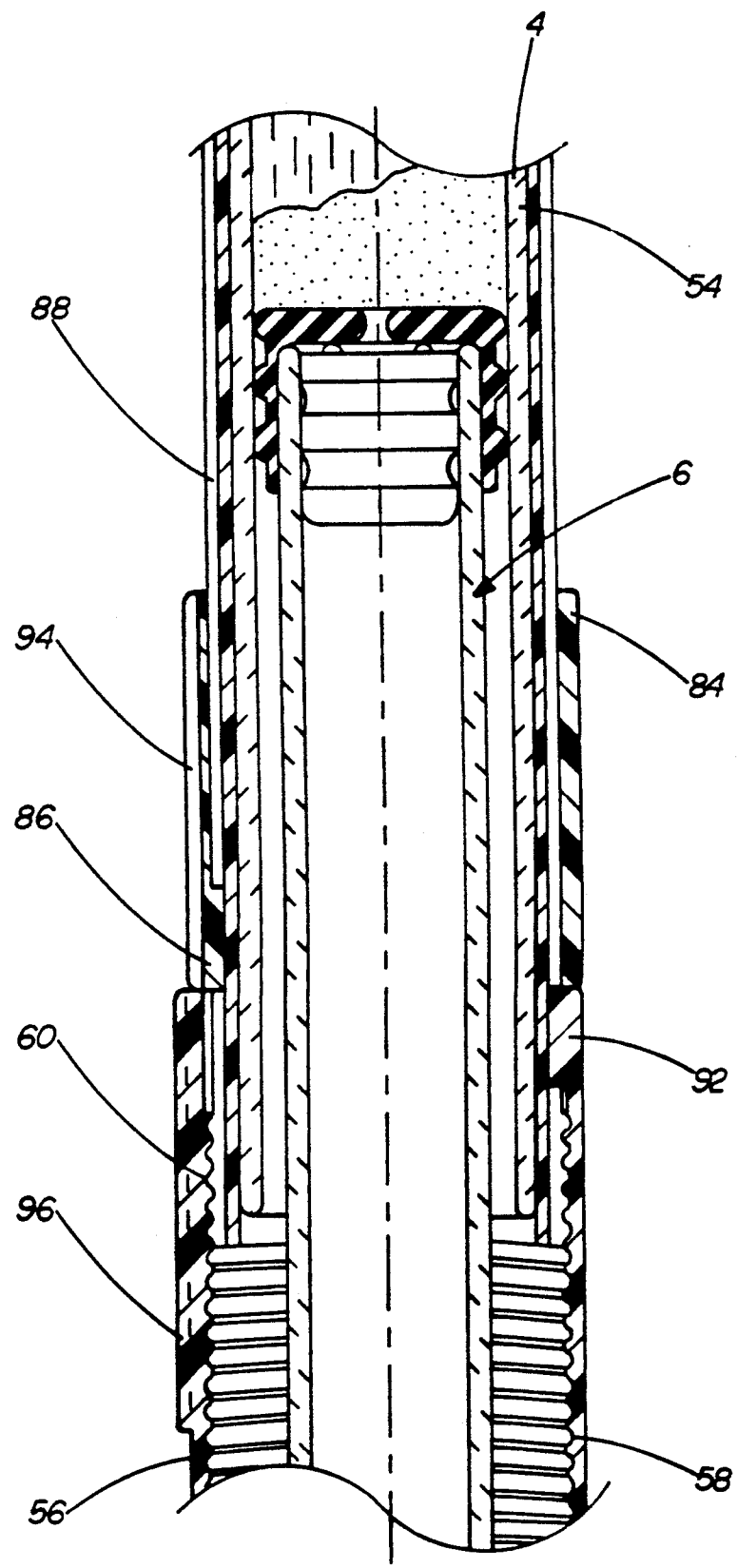
FIG. 5B is an enlarged cross-sectional view of a portion of the assembly of FIG. 5A.

Referring the reader now to FIGS. 1–3, a telescoping, pharmaceutical mixing container 2 is shown to include an outer container 4 and an inner container 6. Outer container 4 has a first end 8 covered by an elastomeric septum 10, the septum held in place by a metal band 12. Outer container 4 also includes an open second end 14 through which inner container 6 extends. Outer container 4 defines a first interior 15 between first and second ends 8, 14.

Inner container 6 includes an open inner end 16 and a closed outer end 18 defining a second interior 20 therein. Inner container 6 also includes a piston 22 which sealingly engages the inner circumferential wall 24 and is free to move along the axis 25 of container 2.

Mixing container 2 also includes a piston cap 26 mounted to inner end 16 of inner container 6. Piston cap 26 has a number of sealing rings 28 which sealingly engage the inner surface 30 of outer container 4. Piston cap 26 defines a flow path 32 which couples a first variable volume portion 34 of first interior 15 defined between piston cap 26 and first end 8, and a second variable volume portion 36 of second interior 20 defined between piston cap 26 and piston 22. Typically, portion 34 contains a pharmaceutical 38 containing both a liquid component 40 and a solid component 42 which has settled out from the pharmaceutical, such as NPH insulin has a tendency to do. To mix pharmaceutical 38, thus dissolving and/or suspending solid component 42 within liquid component 40, container 2 is moved between the extended position of FIG. 1 and the collapsed position of FIG. 2 by alternatingly collapsing container 2 by pressing on the ends of container 2 as suggested by arrows in FIG. 2 and releasing container 2. Releasing container 2 causes the compressed gas within a spring region 44 of second interior 20, defined between piston 22 and end 18, to force piston 22 back towards piston cap 26 when the ends of container 2 are released. The number of mixing cycles required depends on several factors, including the difficulty of redissolving and/or resuspending solid component 42, the degree of mixing required, the amount of turbulence induced in the mixing, and so forth. FIG. 3 illustrates container 2 with pharmaceutical 38 fully mixed and ready for use.

Pharmaceutical 38 can be withdrawn by inserting a needle cannula of a syringe through septum 10 to withdraw the pharmaceutical 38 for injection. Alternatively, container 2 could be mounted within a syringe structure of the type having a double ended needle assembly, one end up which would pierce the septum 10 so that pressing on outer end 18 of inner container 6 would cause the mixed pharmaceutical to be injected through the double ended needle.

FIGS. 4A–6C illustrate a combined mixing container with metering assembly 50 which includes a mixing container 2 and a metering assembly 52. Metering assembly 52 includes an inner sleeve 54, extending along the length of and secured to outer container 4, such as through a friction fit or using an adhesive, and an outer sleeve 56, having internal threads 58 along substantially its entire length. Internal threads 58 are engaged by external threads 60 formed at an inner end 62 of inner sleeve 54. A sealing cap 64 is mounted to the threaded outer end 66 of inner sleeve 54 so to cover septum 10. Cap 64 includes a pocket clip 68 to permit combined assembly 50 to be carried in one's shirt or a jacket pocket if desired.

Combined assembly 50 also includes a driver 70 secured to the outer end 18 of inner container 6, typically with an adhesive. Driver 70 includes a drive stop flange 72 positioned to engage a metering stop flange 74 at the outer end 76 of outer sleeve 56. The inner end 78 of driver 70 has a cup-shaped depression for engagement with outer end 18 of inner container 6. Inner end 78 also includes a radially extending flange 80 which engages metering stop flange 74 to prevent the complete removal of driver 70 from outer sleeve 56. End 78 has one or more slots 82 to permit insertion of inner end 78 into the interior of outer sleeve 56 past metering stop flange 74 during assembly.

Combined assembly 50 also includes a zeroing ring 84 which rides over inner sleeve 54. Ring 84 includes a radially inwardly extending detent 86 which engages one of five circumferentially equally spaced, axially extending grooves 88 formed in outer surface 90 of inner sleeve 54. Likewise, outer sleeve 56 has a radially inwardly extending detent 92 which engages grooves 88 to provide the user with both a tactile and an aural indication of the amount of rotary movement of outer sleeve 56 relative to inner sleeve 54, and thus an indication of the axial displacement of metering stop flange 74 relative to drive stop flange 72. In the preferred embodiment rotation of outer sleeve 56 one groove, corresponding to one-fifth of a complete rotation, corresponds to two units of pharmaceutical 38 to be injected; this is discussed below with reference to FIGS. 6A–6C which illustrate the use of combined assembly 50.

Figure 6A:
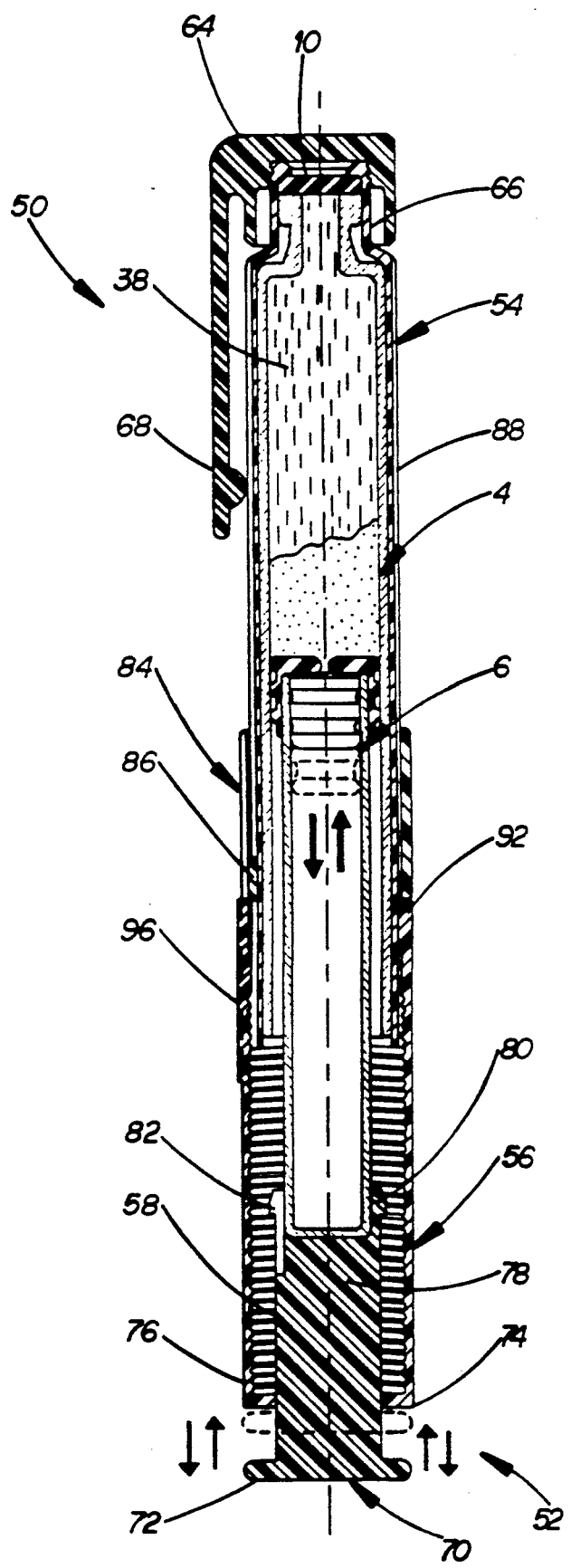
FIG. 6A shows the assembly of FIG. 5A with the outer sleeve threaded three or four full turns over the outside of the inner sleeve to permit the driver to be actuated to mix the pharmaceutical as indicated by the arrows.

To mix pharmaceutical 38 using combined assembly 50, the user first rotates outer sleeve 56 onto inner sleeve 54 several times as shown in FIG. 6A. This provides a sufficient distance between drive stop flange 72 and metering stop flange 74 to permit inner container 6 to be moved between the extended and collapsed positions of FIGS. 1 and 2 thus mixing pharmaceutical 38 as discussed above. After this mixing, outer sleeve 56 is rotated until metering stop flange 74 just contacts drive stop flange 72. At this time zeroing ring 84 is slid axially back against outer sleeve 56 and rotated to align zero markings 94, 96 formed on zeroing ring 84 and outer sleeve 56 respectively. See FIG. 4A. Outer sleeve 56 is then rotated back onto inner sleeve 54. The amount of movement is indicated by the audible and tactile detenting action between detent 92 and grooves 88 as well as by markings 98 on zeroing ring 84 (which slides axially along inner sleeve 54).

Figure 6B:
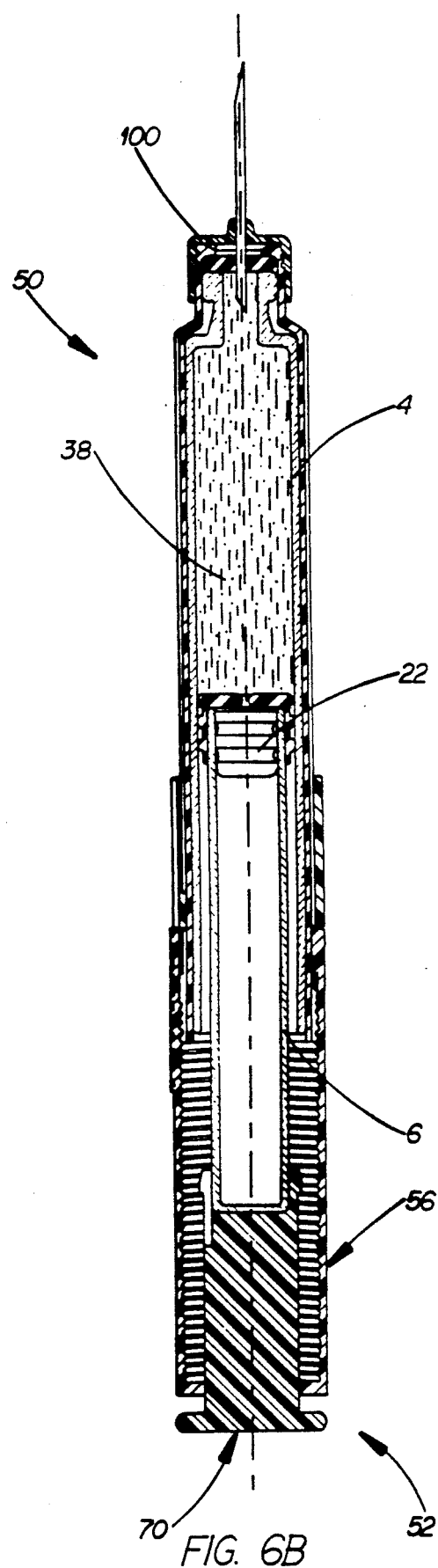
FIG. 6B illustrates the assembly of FIG. 6A after the outer sleeve has been moved back to zero (with the metering stop of the outer sleeve engaging drive stop of the driver) and then rotated according to the amount of the pharmaceutical to be injected as indicated by the detent carried by the outer sleeve engaging the axially extending grooves on the inner sleeve and indicated by the alignment of markings on the outer sleeve relative to the zero marking on the axially floating zeroing ring.

FIG. 6B illustrates the movement of outer sleeve 56 ten clicks or detents, each click or detent corresponding to 2 units of pharmaceutical 38 to be injected. Also, FIG. 6B illustrates that cap 64 has been removed and replaced by a double ended needle assembly 100. The injection can now be given by pressing on driver 70 until drive stop flange 72 engages metering stop flange 74 causing the desired amount of pharmaceutical 38 to be injected.

Figure 6C:
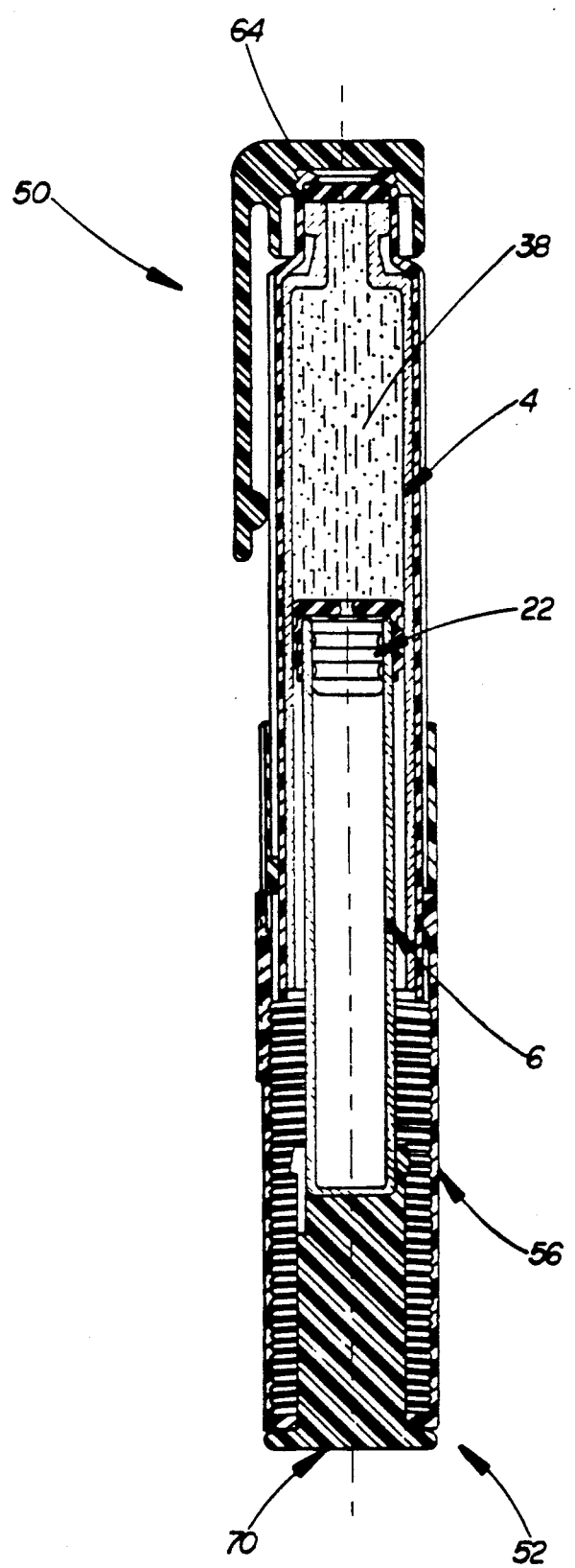
FIG. 6C shows the assembly of FIG. 6B after the injection with the needle assembly removed and the cap replaced.

After the injection is given, needle assembly 100 is removed and cap 64 is replaced as indicated in FIG. 6C. The entire process is repeated for the next injection.

It is preferred that inner and outer containers 4, 6 be made of pharmaceutically compatible glass while septum 10, piston cap 26, and piston 22 are all made of pharmaceutically compatible elastomeric materials.

Inner and outer sleeves 54, 66 are preferably a polymer material, such as polycarbonate, which is sufficiently transparent to enable the user to visually inspect the mixing container 2, especially the condition of pharmaceutical 38.

Modification and variation can be made to the disclosed embodiment without departing from the subject of the invention as defined in the following claims. For example, metering assembly 52 could be used with a generally conventional pharmaceutical cartridge, thus substituting a conventional stem and piston for inner container 6, piston cap 26 and piston 22. Such a structure would obtain the benefits of metering assembly 52 while giving up the benefits of mixing container 2. Inner sleeve 54 could be made as an integral part of outer container 4.

What is claimed is:

1. A telescoping, pharmaceutical mixing container comprising:
    an outer container including a first end, an open second end and defining a first interior therein;
    an inner container extending through the second end and into the first interior for telescopic movement within the first interior between an extended position and a collapsed position, the inner container including an inner end within the first interior, an outer end, and defining a second interior therein;
    a piston housed within the second interior movable along a piston path extending between the inner and outer ends to define a second variable volume portion of the second interior between the piston and the inner end;
    a piston seal carried by the inner container which seals the first interior to create a first variable volume portion of the first interior between the piston seal and the first end as the inner container and piston seal therewith move between the extended and collapsed positions; and
    a flow path element at the inner end of the inner container fluidly coupling the first and second variable volume portions;
    whereby movement of the inner container between the extended and collapsed positions causes fluid movement of a fluid pharmaceutical between the first and second variable volume portions with resultant mixing of said pharmaceutical.

2. The container of claim 1 wherein the outer container has a pierceable septum at the first end.

3. The container of claim 2 further comprising a double ended needle assembly, the first end of the outer container being adapted to receive the double ended needle assembly so the container can be used as a syringe.

4. The container of claim 1 wherein the inner container and the piston define a third variable volume portion of the second interior between the piston and the outer end, said third variable volume portion being a sealed region so that movement of the piston towards the outer end compresses any gas within the third variable volume portion so that the inner container is biased towards the extended position when at the collapsed position.

5. The container of claim 1 wherein the outer container is a cylindrical tube-like structure.

6. The container of claim 5 wherein the inner container is cylindrical.

7. The container of claim 1 wherein the piston seal and the flow path element are made from a one-piece piston cap element mounted over the inner end of the inner container.

8. A telescoping, pharmaceutical mixing container comprising:
    inner and outer telescoping containers, the inner container including an inner end, housed within the outer container, and an outer end;
    means for telescopically sealing the inner container within the outer container as the inner container moves between extended and collapsed positions so to create a first variable region within the outer container;
    a piston movably housed within the inner container, the piston defining a second variable volume region between the piston and the inner end; and
    a flow path element fluidly coupling the first and second variable volume regions;
    whereby a flowable pharmaceutical within at least one of the first and second variable volume regions is mixed by passing through the flow path as the inner container moves between the extended and collapsed positions.

9. The container of claim 8 wherein the inner container includes means for biasing the piston towards the inner end when the inner container is in the collapsed position.

10. The container of claim 8 wherein the biasing means is a compressed gas biasing means.

11. The container of claim 8 further comprising:
    means, movably mounted to the outer container, for positioning a metering stop at a chosen position relative to the inner container; and
    the inner container including a driver at the outer end, the driver including a drive stop positioned to engage the metering stop as the inner container moves towards the collapsed position thereby limiting the movement of the inner container.

12. The container of claim 11 wherein the positioning means includes means for threadably mounting the metering stop to the outer container.

13. The container of claim 12 wherein the positioning means includes means for mechanically indicating the axial movement of the metering stop relative to the outer container.

14. The container of claim 13 wherein the mechanical movement indicating means includes detent means for providing tactile and auditory indications of the axial movement of the metering stop relative to the outer container.

15. The container of claim 11 wherein the outer container includes a first end and a second end through which the inner container passes, and further comprising a cap removably mounted to the first end of the outer container.

16. The container of claim 12 wherein the threadably mounting means includes:
    an inner sleeve secured to the outer container, the inner sleeve including an external threaded portion; and
    an outer sleeve, the outer sleeve including internal threads which engage the external threaded portion.

17. The container of claim 16 wherein one of the inner and outer sleeves include a series of axially extending, circumferentially spaced elements which are engaged by a radially extending element of the other of the inner and outer sleeves so to provide a mechanical indication of the movement of the outer sleeve.

18. The container of claim 17 wherein the inner container further comprises means for biasing the piston towards the inner end.

19. A combined pharmaceutical mixing container and metering assembly comprising:
   inner and outer telescoping containers, the inner container including an inner end, housed within the outer container, and an outer end;
   means for telescopically sealing the inner container within the outer container as the inner container moves between extended and collapsed positions so to create a first variable region within the outer container;
   a piston movably housed within the inner container, the piston defining a second variable volume region between the piston and the inner end;
   a flow path element fluidly coupling the first and second variable volume regions;
   means for biasing the piston towards the inner end when the inner container is in the collapsed position;
   means, threadably mounted to the outer container, for positioning a metering stop at a chosen position relative to the inner container;
   the positioning means including:
   detent means for providing tactile and auditory indications of the axial movement of the metering stop relative to the outer container;
   an inner sleeve secured to the outer container, the inner sleeve including an external threaded portion;
   an outer sleeve, the outer sleeve including internal threads which engage the external threaded portion; and
   one of the inner and outer sleeves including a series of axially extending, circumferentially spaced elements which are engaged by a radially extending element of the other of the inner and outer sleeves so to provide a mechanical indication of the movement of the outer sleeve; and
   the inner container including a driver at the outer end, the driver including a drive stop positioned to engage the metering stop as the inner container moves towards the collapsed position thereby limiting the movement of the inner container;
   whereby a flowable pharmaceutical within at least one of the first and second variable volume regions is mixed by passing through the flow path as the inner container moves between the extended and collapsed positions.

* * * * *